United States Patent [19]
Huang et al.

[11] Patent Number: 5,362,860
[45] Date of Patent: Nov. 8, 1994

[54] NEUTRAL STABILIZATION COMPLEX FOR CI-979 HCL, A COGNITION ACTIVATOR

[75] Inventors: Hua-Pin Huang, Succasunna; Scott C. Wootton, Liberty Corner; Thomas N. Julian, Annandale; Galen W. Radebaugh, Chester; Mahdi B. Fawzi, Flanders, all of N.J.

[73] Assignee: Warner-Lambert Company, Morris Plains, N.J.

[21] Appl. No.: 12,107

[22] Filed: Feb. 1, 1993

[51] Int. Cl.$^5$ .................. C07G 3/00; C07G 11/00; C07H 15/00; A01N 43/40
[52] U.S. Cl. ........................ 536/4.1; 536/103
[58] Field of Search ............... 536/4.1, 103; 514/357

[56] References Cited

U.S. PATENT DOCUMENTS

| | | | |
|---|---|---|---|
| 4,555,504 | 11/1985 | Jones | 536/103 |
| 4,710,508 | 12/1987 | Bergmeier et al. | 514/357 |
| 4,786,648 | 11/1988 | Bergmeier et al. | 546/333 |
| 4,834,985 | 5/1989 | Elger et al. | 424/488 |

FOREIGN PATENT DOCUMENTS

0494057  8/1991  European Pat. Off. .

OTHER PUBLICATIONS

S. El Gezawi, N. Omar, N. Elrabbat, H. Ueda, and J. H. Perrin. "Microcalorimetric and chromatographic investigations of the binding of some pyridine derivatives to cyclodextrins". *Journal of Pharmaceutical & Biomedial Analysis*, vol. 6, No. 4, pp. 399–406 (1988).

Dominque Duchene and Denis Wouessidjewe. "Physiocochemical Characteristics and Pharmaceutical Uses of Cyclodextrin Derivatieves, Part II". *Pharmaceutical Technology*, Aug. 1990.

J. Szejtli. "Cyclodextrins in Drug Formulations: Part II". *Pharmaceutical Technology*, Aug. 1991.

Thorsteinn Loftsson and Birna J. Olafsdottir. "Cyclodextrin-accelerated degradation of B-lactam antibiotics in aqueous solutions". *International Journal of Pharmaceutics*, 67 (1991) R5–R7.

A. S. Kearney, S. C. Mehta, and G. W. Radebaugh. "The effect of cyclodextrins on the rate of intrmaolecular lactamization of gabapentin in aqueous solution". *International Journal of Pharmaceutics*, 78 (1992) 25–34.

Primary Examiner—Nathan M. Nutter
Attorney, Agent, or Firm—Michael J. Atkins

[57] ABSTRACT

A solid composition for stabilizing the dosage of cognition activator CI-979 HCl by formation of a complex with cyclic polydextrose. In particular, compositions with HP$\beta$CD have been found to stabilize CI-979 HCl even in the presence of other excipients such as sodium carbonate. Pharmaceutical formulations for the treatment of cognitive disorders in humans are based on the stabilizing composition of CI-979 HCl and cyclic polydextrose, including appropriate amounts of other excipients or components as known in the formulation art.

12 Claims, No Drawings

NEUTRAL STABILIZATION COMPLEX FOR CI-979 HCL, A COGNITION ACTIVATOR

This invention is related generally to a stabilized composition and more particularly a solid storage complex of pyridine based oximes. Further, such a composition is useful for stabilizing the cognition activating drug CI-979 HCl, against losses to degradation or evaporation.

BACKGROUND OF THE INVENTION

Disorders of cognition are generally accompanied by symptoms of forgetfulness, confusion, memory loss, and other aspects as a result of aging, brain injury or disease. The concomitant decrease in cognitive function during the aging process has been documented in various mammals and more recently in human subjects as well. In particular, presenile and senile primary degenerative dementia appear to be common causes of mental deterioration among the elderly. In fact, the symptoms of cognitive disorder appear to be associated with decreased acetyl chlorine synthesis as well as impairment of the choline receptive neurons. Especially, the activity of the enzyme choline acetyl transferase (CAT) which catalyzes the synthesis of acetyl choline from its previous choline and acetyl coenzyme A can be severely reduced as reflected by the loss of cholinergic (acetyl choline releasing) nerve ending in the hippocampus. The cholinergic terminals are recognized as critically important to memory function.

The alkaloid arecoline (methyl ester of 1-methyl-1,2,5,6-tetrahydropiperidine-3-carboxylic acid) which is isolated from betel nuts is well-known as to its mucscarinic effects. However, arecoline is toxic to mammals and therefore limited to veterinary anthelmintic use. Certain alkaloid derivatives, such as O-substituted 1,2,5,6,-tetrahydropyridine oximes, have shown pharmacological properties useful for therapy of age-associated memory impairment and primary degenerative dementia. In particular, the drug CI-979 has been described, inter alia, in U.S. Pat. No. 4,786,648, which disclosure is incorporated herein by reference, as a cognition activator presently under development for the treatment of Alzheimer's disease.

The compound CI-979 HCl has the following structural formula (Ia)

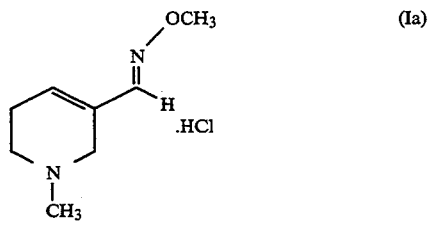

As can be seen from formula (Ia), CI-979 contains a methyloxime group attached to a basic tetrahydropyridine ring to form 1,2,5,6-tetrahydro-1-methyl-3-pyridine carboxaldehyde O-methyloxime. Similar to other pyridine derivatives, the free base form, CI-979, is an oily liquid which is volatile, whereas the CI-979 monohydrochloride is a stable white crystalline salt having a m.p. of 218°-219° C.

The storage stability of the drug has been tested by exposure to heat, UV light, and the extremes of the pH range. While the CI-979 HCl bulk drug is stable for at least six weeks at high temperature and high humidity, it was found that under similar storage conditions a significant drug loss recurred from some solid formulations. In particular, results from excipient compatibility studies show that the HCl salt converts to the volatile free base in the presence of a basic or neutral solid excipient and may, consequently, be lost from the solid composition by evaporation.

Conversely, in acidic environments of less than about pH 5, the drug has been found to undergo hydrolysis, thereby forming an aldehyde degradation product (A) which is biologically inactive.

Two major degradation pathways have been proposed for CI-979 HCl. One pathway represents the hydrolysis to the aldehyde compound (A), 1,2,5,6-tetrahydro-1-methyl-3-pyridine carboxaldehyde, under acidic (i.e. <pH 5) conditions. The second pathway consists of isomerization to the syn- (or Z-) isomer of CI-979 by exposure to UV light.

In particular, hydrolysis of CI-979 to the aldehyde form is a temperature dependent first-order reaction. The light-catalyzed reaction of CI-979 HCl in solution is apparently somewhat pH-dependent, with the highest rate of isomerization occurring at about pH 8.0. The UV light energy presumably weakens the oxime double bond and potentiates rotation to a thermodynamically less stable state.

Moreover, the alkaloid drug, CI-979 HCl, has been found to be labile in acidic or neutral, only slightly humid microenvironment, even in the solid state, a microenvironment being defined as the ambient conditions surrounding a given molecular aggregate or agglomerate. In fact, CI-979 HCl undergoes hydrolysis as a solid mixture formulated in bulk with polyhydroxy excipients. However, only minimal isomerization has been observed as measured by reverse phase high performance liquid chromatography.

Consequently, the storage stability problem of the drug as a solid formulation represented a two-fold dilemma. On the one hand, an acid microenvironment would cause hydrolysis of CI-979 HCl, although prevent conversion of the HCl-salt to the free base and subsequent volatilization. On the other hand, an alkaline microenvironment would diminish CI-979 degradation but allow formation of the volatile free base of the drug.

It is well-known to the skilled in the art that cyclic polydextrose molecules such as cyclodextrin and derivatives thereof, tend to entrap other, smaller molecules thereby endowing such trapped molecules with certain new physicochemical or pharmacotechnical properties. For example cyclodextrins can be used to stabilize certain liquids or oils by effecting their transformation into solid forms or stabilize products susceptible to oxidation, evaporation, or other reactions in air, light or heat. Cyclodextrins are also known to stabilize some products susceptible to hydrolysis. Generally, however, the main utility of cyclodextrins ("CD") may be found in the increased solubility of drug-cyclodextrin complexes in water, thus improving the bioavailability of the drug. See D. Duchene, et al. "Physicochemical characteristics and Pharmaceutical Uses of Cyclodextrin Derivatives Part II," *Pharmaceutical Technology* (August 1990) p. 22.; J Szejtli, "Cyclodextrins in Drug Formulations: Part II," *Pharmaceutical Technology* (August 1991) p. 24–30.

It is known, therefore, that CD complexes of hydrophobic drugs in solid dosage form offer improved drug stability resulting in longer shelf life. Lipophilic drugs, in CD complexed form, show increased bioavailability compared to the non-complexed or free forms while reducing local irritation and time for solubilization of the drugs. But CD complexation is not always so advantageous.

On the contrary, certain β and γ cyclodextrins have been found to have an accelerating effect on the rate of degeneration of certain β-lactam antibiotics (T. Loftsson et. al. 1991, *International J. Pharmaceutics* 67 R5-R7). In addition, the lactamization rate (intramolecular aminolysis) of aqueous solutions of gabapentin (a GABA-derivative) was accelerated in the presence of HPβCD and other types of cyclodextrins. None of the various cyclodextrins thus investigated appeared to stabilize gabapentin.

Hydroxypropyl β-cyclodextrin (HPβCD) has been reported as useful in parental formulations of alfasalone, carbonazepine, and dexamethasone. In addition, delivery systems of gonadal steroids and steroid derivatives using HPβCD complexes have been studied in animals.

In view of the conflicting evidence from the literature in this field, therefore, the effect of the interaction of the CD moieties with alkaloid methyloximes such as CI-979 HCl in solid formulations has been unpredictable. In fact, CD complexation of numerous drugs has been studied over a number of years but only a few drug-CD complexes resulted in advantageous or useful medical products in terms of enhanced stability, bioavailability, or dosage of the drug.

It is therefore the object of the present invention to provide a solid composition for stabilizing certain alkaloid methyloximes, such as the cognition activating agent, CI-979 HCl. In particular, it is the object of the present invention to provide a solid neutral excipient such as polycyclodextrose which simultaneously avoids hydrolytic degradation and neutral/base volatilization of the alkaloid drug.

SUMMARY OF INVENTION

It has now been discovered that cyclic polydextrose provides a stable solid inclusion complex with an O-substituted tetrahydropyridine oxime, such as CI-979 HCl, defined above. This solid complex stabilizes the alkaloid drug thereby resulting in a significant reduction of volatilization or hydrolysis degradation even under severely accelerated storage conditions.

Accordingly, the present invention provides a stable solid composition for the treatment of cognition impairment in animals or humans comprising a cyclodextrin complex with the active compound CI-979 HCl.

More particularly, the stable storage complex according to the present invention is directed to a tetrahydropyridine oxime such as CI-979 HCl in combination with modified cyclodextrin such as hydroxypropyl β-cyclodextrin.

The present invention is therefore suitable for providing cognition activating compositions comprising the active ingredient, CI-979 HCl, which is stabilized in an inclusion - complex with a cyclopolydextrose.

Specifically, a preferred embodiment of the present invention is directed to a solid pharmaceutical formulation that contains a cyclic polydextrose such as HPβCD in a complex with CI-979 HCl at a molar ratio of about 13 to 1, respectively.

Further to the present invention, a stable complex of CI-979 with solid polydextrose can be utilized by pharmaceutical formulations, e.g., in the form of capsules or tablets for therapy.

DETAILED DESCRIPTION OF THE INVENTION

It has now been surprisingly discovered that pyridine derivatives such 1,2,5,6-tetrahydro pyridines are advantageously and significantly stabilized by solid polydextrose complexing agents. In particular, it was found that the drug CI-979 HCl exhibits adequate stability when complexed with hydroxypropyl β-cyclodextrin (HPβCD; ENCAPSIN TM). Under accelerated stress conditions, the inventive composition registered virtually no activity losses and provided advantageously greater stability in comparison with other excipients with similar near neutral pH values.

As shown in Table I, comparative studies revealed that CI-979 HCl/HPβCD complexes retained 96% of the active compound after 10 days at 60° C. and still 95% of the active compound after 17 days at 60° C.

The amount of CI-979 free base in the samples was calculated by comparison of the peak areas of the samples with that of the external standard. Lacking pure samples of the potential degradation products area normalization was applied to estimate degradation products of CI-979, as shown in Table I.

Further aspects of the present invention can be seen from Examples 1, 2 and 3, described below.

TABLE I

| | | | Recovery of CI-979 HCl after storage at 60° C. for 10 and 17 days | | | | | |
|---|---|---|---|---|---|---|---|---|
| | | | 10 days at 60° C. | | | 17 days at 60° C. | | |
| Excipient | pH[1] | Initial Assay[2] | % CI-979 Remaining[3] | % aldehyde (A) Present[4] | Total | % CI-979 Remaining[3] | % aldehyde (A) Present[4] | Total |
| Adipic Acid | 2.5 | 101 | 84 | 4 | 88 | 85 | 3 | 88 |
| Fumaric Acid | 2.3 | 100 | 90 | 2 | 92 | 88 | 2 | 90 |
| Succinic Acid | 2.3 | 100 | 64 | 14 | 78 | 71 | 7 | 78 |
| Gentisic Acid | 2.1 | 99 | 69 | 45 | 114 | 61 | 34 | 95 |
| Alginic Acid | 2.7 | 80 | 18 | 65 | 83 | — | — | — |
| Sodium Phosphate Monobasic | 3.3 | 99 | 44 | 35 | 79 | 23 | 35 | 58 |
| PVP K29/32 | 4.0 | 100 | 78 | 0 | 78 | 73 | 0 | 73 |
| Lactose, Anhydrous NF | 4.5 | 101 | 87 | 0 | 87 | 84 | 0 | 84 |
| Sugar granular NF | 5.2 | 102 | 87 | 2 | 89 | 83 | 2 | 85 |
| Non-pareil Seeds | 5.7 | 99 | 74 | 0 | 74 | 89 | 0 | 89 |
| Eudragit L100 | 5.8 | 99 | 62 | 14 | 76 | — | — | — |
| Avicel PH 101 | 5.9 | 71 | 110 | 0 | 110 | — | — | — |
| HPβCD (Encapsin) | 6.2 | 101 | 96 | 0 | 96 | 95 | 0 | 95 |
| Corn Starch NF | 6.3 | 98 | 95 | 0 | 95 | 92 | 2 | 95 |

TABLE I-continued

| | | | Recovery of CI-979 HCl after storage at 60° C. for 10 and 17 days | | | | | |
|---|---|---|---|---|---|---|---|---|
| | | | 10 days at 60° C. | | | 17 days at 60° C. | | |
| Excipient | pH[1] | Initial Assay[2] | % CI-979 Remaining[3] | % aldehyde (A) Present[4] | Total | % CI-979 Remaining[3] | % aldehyde (A) Present[4] | Total |
| Sephadex G50 | 6.5 | 93 | 75 | 0 | 75 | 11 | 0 | 11 |
| HPC (Klucel EF) | 7.1 | 100 | 57 | 0 | 57 | 55 | 0 | 55 |
| Sodium Phosphate Dibasic | 8.9 | 102 | 4 | 0 | 4 | 2 | 0.5 | 2.5 |
| Carrageenan | 10.1 | 63 | 7 | 0 | 0 | — | — | — |

[1]pH of a saturated aqueous suspension of the excipient alone. For PVP, Klucel and Carrageenan, the pH was determined before they became too viscous (ca. 5 to 10%).
[2]% CI-979, based on theoretical.
[3]Based on initial assay.
[4]Based on the maximum theoretical amount that could be found.

EXAMPLE 1 (TABLE I)

Example 1 relates to a comparative two-component drug compatibility study using various excipients and testing the resulting stability under accelerated conditions, shown in Table I. Excipients used included: a) adipic acid, b) fumaric acid, c) succinic acid, d) gentisic acid, e) alginic acid, f) sodium phosphate monobasic, g) PVP, h) lactose, anhydrous, i) sugar, granular, j) nonpareil seeds k) eudragit, l) avicel, m) hydroxy β-cyclodextrin (HPβCD), n) corn starch, o) sephadex G50, p) hydroxypropyl cellulose (HPC), q) sodium phosphate, dibasic, and r) carrageenan.

In fact, the amount of aldehyde degradation product was less than 1% (w/w) in all cases. These advantageously stable complexes, therefore, can be predicted to allow further optional variations of the solid storage formulation of CI-979 HCl.

An aliquot of a drug solution containing 0.5 mg of CI-979 HCl was mixed with 200 mg of excipient and placed in an oven at 60° C. for 10 and 17 days. Percent CI-979 remaining and the aldehyde breakdown product of hydrolysis obtained were recorded as compared with the initial assay by reverse phase high performance liquid chromatography.

The reverse phase high performance liquid chromatography (HPLC) procedure described below was used to measure the concentrations of CI-979 and the breakdown products of stored formulations of the drug. The HPLC system consisted of a Hewlett-Packard 1090 Liquid Chromatograph equipped with Beckman Digimetry MKS Instrument Coupler and a Kratos model 783 detector operated at a fixed wavelength of 225 nm. The column bed was Zorbax CN, 5 mm, 250 mm×4.6 mm i.d. An aqueous buffer of 0.001M Pic B8 ® (octanesulfonic acid), 0.00025M Triethylamine was adjusted to pH 3.0 with $H_3PO_4$ and modified with Acetonitrile in the mobile phase to 99:1 ratio (Buffer: Modifier) with an eluant flow rate of 1.3 ml/min for 15 min run time. The injection volume was 20 μl. The retention times were found approximately 3.8 min for or 1,2,5,6-tetrahydro-1-methyl-3-pyridine carboxylic acid, 4.6 min for 1,2,5,6-tetrahydro-1-methyl-3-pyridine carboxaldehyde, 9.6 min for the Z-isomer of CI-979, and 10.5 min for CI-979.

A standard reference solution of analytically pure CI-979 HCl was prepared at a final concentration of 0.02 mg/ml. Samples were prepared by weighing aliquots of approximately 100 mg of the CI-979 HCl/excipient mixture (equivalent to approximately 1.0 mg CI-979 HCl), dissolving it in water and diluting the solution to a concentration of about 0.02 mg/ml. For drug/dibasic sodium phosphate samples, 1N HCl was used to dissolve the drug and to neutralize the sample solution. Samples that were not soluble in water were filtered through a 0.45 μm syringeless glass microfiber filter (Genex, Inc.) before HPLC assay. The drug was shown not to adsorb to the filter. Interference from soluble excipients in the sample solutions was not observed in any of the HPLC chromatograms. Percent CI-979 remaining was calculated with reference to initial values. Percent of the aldehyde breakdown product was calculated based upon the maximum theoretical amount that could be formed if 100% of the parent compound was hydrolyzed. The quantities (w/w percent) of CI-979 remaining after storage, with different solid excipients, are listed in Table I. The pH values of a saturated solution of the excipients are also listed in Table I. Percent aldehyde breakdown product was calculated based on the total amount of the aldehyde form which theoretically could be generated from CI-979 HCl. HPβCD provided the best recovery of the drug in the excipients studied.

Since it was previously established in a comparative series of experiments that the dry loss from HPβCD complexes is less than 2% under all kinds of humidity at ambient temperature, the stability of CI-979 HCl salt was studied in the presence of basic excipients.

The advantageous stabilizing effect on the storage of CI-979 complexed with HPβCD was further studied in the presence of other additional excipients. For example, a comparative study described below demonstrated that HPβCD complexation affords an advantageous stability to CI-979 even when stored in composition with a basic excipient.

EXAMPLE 2 (TABLE II)

Sodium carbonate was selected as the model basic excipient to conduct accelerated drug stability studies. For that purpose, one milligram of CI-979 HCl, 30 mg of excipient and 200 mg of sodium carbonate were mixed and placed in an oven at 60° C. for 20 hours. The excipients other than HPβCD included a) corn starch, b) sugar, c) ethylcellulose, d) hydroxymethyl cellulose (HPMC), e) polyethylene glycol, and f) sodium lauryl sulfate. As indicated in Table II, the HPβCD complex improved the stability of CI-979 in the presence of sodium carbonate. The stabilizing effect from other polysaccharide excipients was varied but distinctly lower. Compared to other polysaccharides in Table 2, HPβCD had apparently functioned as more than just a diluent. Indeed, these results suggest that the drug may have formed an inclusion complex with HPβCD and become less volatile. Specifically, no degradation product was detected by reverse phase high performance liquid chromatography (HPLC), according to the method disclosed above. (Example 1). (See Table II). For example, despite the presence of sodium carbonate HPβCD retained 86% CI-979 HCl in a complex after 20 h at 60° C.

TABLE II

Percent CI-979 Remaining after Storage 60° C. for 20 hours.

| CI-979 HCL (mg) | Excipient (30 mg) | Sodium Carbonate (mg) | Percent CI-979 Remaining |
|---|---|---|---|
| 1 | none | 200 | 2 |
| 1 | HPBCD | 200 | 86 |
| 1 | Corn Starch NF | 200 | 5 |
| 1 | Sugar, NF | 200 | 6 |
| 1 | Ethylcellulose NF | 200 | 44 |
| 1 | HPMC NF | 200 | 24 |
| 1 | PEG 3350 | 200 | 41 |
| 1 | SLS NF | 200 | 67 |

[1]Based on theoretical.

EXAMPLE 3 (TABLES III AND IV)

Moreover, a 20 hour storage test at 60° C. demonstrated that the stability of a CI-979 HCl complex with excipient HPβCD increases as the inverse ratio (w/w) of the drug CI-979 to the excipient HPβCD in the presence of sodium carbonate.

The factors affecting the loss of CI-979 HCl from solid formulations were evaluated to account for the mass imbalance observed in previous preformulation studies. In particular, it was apparent that the drug was lost at a faster rate from basic excipients, in open containers, and in presence of water. It was speculated that, in the presence of basic excipients and water, CI-979 HCl converted to the free base and subsequently was lost by evaporation since CI-979 free base is a volatile liquid, as described above. This hypothesis was tested by enclosing CI-979 salt, mixed with sodium carbonate and water, in a sealed container with a trap to collect CI-979 free base and stored at 60° C. The amount of the HCl salt remaining and the free base generated was 41.7% and 47.7%, respectively, indicating clearly that significant loss of CI-979 HCl occurred by volatilization in the presence of sodium carbonate, a basic excipient, and water.

To determine the effect of HPβCD concentrations on the stability of CI-979, drug recovery in presence of both sodium carbonate and different levels of HPβCD was also evaluated. As shown in Tables III and IV, the stabilizing effect of HPβCD increases with increasing amounts of HPβCD added to the drug/HPβCD/sodium carbonate mixture. The stability profiles exhibit an initial linear relationship and indicate that mixtures containing a CI-979 HCl: sodium carbonate ratio of 1 to 200 (w/w) were more stable than the 1:400 ratio samples. The lack of plateau of the lower curve also indicates that maximum protection of the drug was not reached before about a 32 to 1 (w/w) ratio of HPβCD to CI-979 HCl. A HPβCD: CI-979 HCl mixture having a ratio (w/w) of 100 to 1 provided complete protection to the drug under the extreme conditions used in this study (CI-979 HCl: sodium carbonate ratio to 1 of 200 w/w). This optimal ratio of HPβCD to CI-979 HCl is equivalent to a molar ratio of about 13 to 1.

TABLE III

Percent CI-979 Remaining after Incubation with HPβCD and Sodium Carbonate at 60° C. for 20 hours.

| CI-979 HCL (mg) | HPβCD (mg) | CI-979 HCl:HPβCD Ratio (w/w) | Sodium Carbonate (mg) | Percent CI-979 Remaining[1] |
|---|---|---|---|---|
| .5 | 0 |  | 200 | 3 |
| .5 | 1 | 1:2 | 200 | 8 |
| .5 | 2 | 1:4 | 200 | 13 |
| .5 | 3 | 1:6 | 200 | 18 |
| .5 | 4 | 1:8 | 200 | 23 |
| .5 | 8 | 1:16 | 200 | 44 |
| .5 | 16 | 1:32 | 200 | 73 |

[1]Based on theoretical.

TABLE IV

Percent CI-979 Remaining after Incubation with HPβCD and Sodium Carbonate at 60° C. for 20 hours.

| CI-979 HCL (mg) | HPβCD (mg) | CI-979 HCl:HPβCD Ratio (w/w) | Sodium Carbonate (mg) | Percent CI-979 Remaining[1] |
|---|---|---|---|---|
| 1 | 0 |  | 200 | 2 |
| 1 | 5 | 1:5 | 200 | 26 |
| 1 | 10 | 1:10 | 200 | 42 |
| 1 | 20 | 1:20 | 200 | 77 |
| 1 | 30 | 1:30 | 200 | 86 |
| 1 | 50 | 1:50 | 200 | 95 |
| 1 | 100 | 1:100 | 200 | 101 |

[1]Based on theoretical.

The results establish even in the presence of sodium carbonate that formulations of CI-979 in HPβCD are particularly stable when the ratio of HPβCD to CI-979 is in the range of about 30:1 to about 100:1 based on the theoretical percent content of CI-979 in the preparation.

In addition, other types of cyclodextrins and their derivatives may be also useful for the stabilization of CI-979 HCl.

TABLE V

| Ingredients | Critical ranges | Preferred ranges |
|---|---|---|
| CI-979 HCl | 0.001–10% | 0.1–1% |
| (HPβCD, or other modified cyclodextrins) | 1–99% | 5–10% |

As shown in Table V, complexes of the drug with HPβCD are apparently effective in the range of about 0.001%–10% (w/w) CI-979 HCl and about 1%–99% HPβCD. The preferred ranges are about 0.1%–1% (w/w) and about 5%–10% (w/w) for CI-979 HCl and HPβCD, respectively.

Any variations of the invention described above are not to be regarded as a departure from the spirit and scope of the invention as claimed.

A stable mixture or a stable triturate of CI-979 HCl and cyclodextrin can be prepared and subjected to further formulation. Further formulation of cyclodextrin stabilized mixtures of CI-979 HCl may include the use of other excipients typically used in the art of formulating pharmaceutical dosage forms. The types of excipients may include, but not be limited to, binders, lubricants, disintegrants and diluents. Specific examples of these excipients are listed in the USP XXII/NFXVII, 1990. The present invention without limiting further provides for diluent additives such as microcrystalline cellulose, hydrous lactose, corn starch, sucrose, silicic anhydride or polysaccharides (as are known as suitable in the art); binders such as methylcellulose, carboxymethylcellulose, hydroxypropylcellulose, hydroxymethylpropylcellulose, polyvinylpyrrolidone, polyvinylalcohol or starch; disintegrants such as carboxymethylcellulose calcium, croscarmellose sodium, or starch; and surfactants such as the non-ionic detergent Tween 80 or polyoxyethylenepolyoxypropylene copolymer. Preferredly, the inventive composition contains a suitable amount of croscarmellose sodium as functional disintegrant and the non-ionic detergent Tween 80 as a surfactant. The composition also contains hydroxypropyl cellulose as binder selected from among several applicable substances such as, i.e., polyethylene glycol, polyvinylpyrrolidone, polyvinyl alcohol, hydroxymethylcellulose or hydroxypropylmethylcellulose. As anti-oxidants, reagents such as butylated hydroxyanisole, sodium ascorbate, ascorbic acid or others may optionally be incorporated in the composition. Magnesium stearate can be selected from a group including other substances such as calcium stearate, stearic acid, palmitic acid, talc or similar lubricating compounds.

Other possible and supplemental ingredients such as preservatives, driers, glidants, or colorants known as conventional by those skilled in the art may be included optionally in the pharmaceutical formulation.

A typical example (Example 4, Table VI) formulation is illustrated below:

TABLE VI

| Component | Percent by weight Formulation | | | |
|---|---|---|---|---|
| | A | B | C | D |
| CI-979 HCl | .001 | .01 | .05 | 1 |
| Cyclodextrin | 5 | 60 | 70 | 50 |
| Croscarmellose | 1 | 2 | 3 | 2 |
| Microcrystalline cellulose | 20 | | 20.95 | |

TABLE VI-continued

| Component | Percent by weight Formulation | | | |
|---|---|---|---|---|
| | A | B | C | D |
| Lactose | 72 | 31.99 | | 42 |
| Povidone | | 5 | | 4 |
| Hydroxypropylmethylcellulose | | | 4 | |
| Calcium Stearate | | | 2 | 1 |
| Magnesium Stearate | 1.999 | 1 | | |

Example 4 is to demonstrate useful pharmaceutical formulations based on the cyclodextrin stabilized compositions of CI-979 HCl for the treatment of cognitive disorders such as Alzheimer's disease. The concentrations are indicated in compositions A, B, C and D as listed in Table VI.

What is claimed is:

1. A solid cholinergic composition comprising in a stable complex an o-substituted 1,2,5,6-tetrahydropyridine oxime alkaloid derivative compound and a cyclic polydextrose excipient, the composition exhibiting a stable release of the o-substituted 1,2,5,6-tetrahydropyridine oxime alkaloid derivative compound when exposed to accelerated storage conditions at temperatures ranging up to about 60° C.

2. The solid cholinergic composition of claim 1 wherein the alkaloid derivatives compound is the 1,2,5,6-tetrahydro-1-methyl-3-pyridine carboxaldehyde methyl oxime hydrochloride, CI-979 HCl, of the structural formula:

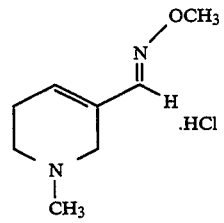

3. The solid cholinergic composition of claim 1 wherein the cyclic polydextrose excipient is a cyclodextrin.

4. The solid cholinergic composition of claim 3 wherein the cyclodextrin is selected from the group consisting of α-cyclodextrin, β-cyclodextrin, γ-cyclodextrin, and hydroxypropyl β-cyclodextrin.

5. The solid composition of claim 2 wherein the compound CI-979 HCl is complexed with hydroxypropyl β-cyclodextrin at a molar ratio of about 1 to 13, respectively.

6. A solid pharmaceutical formulation for the treatment of cognition impairment comprising a therapeutically effective amount of the compound CI-979 HCl of claim 2 and a cyclic polydextrose.

7. The solid pharmaceutical formulation of claim 6 which comprises a triturate preparation.

8. The solid pharmaceutical formulation of claim 6 wherein the cyclic polydextrose comprises HPβCD in a complex with the compound CI-979 HCl, at a molar ratio of about 13 to 1, respectively.

9. A method for stabilizing the o-substituted 1,2,5,6-tetrahydropyridine oxime alkaloid derivative compound in a solid composition comprising combining the compound with a cyclic polydextrose excipient in molar ratio of about 1 to 13 such that the composition exhibits a stable release of the o-substituted 1,2,5,6-tetrahydropyridine oxime alkaloid derivative compound when exposed to accelerated storage conditions at temperatures ranging up to about 60° C.

10. The method of claim 9 wherein the combining step is performed by triturating the compound with the cyclic polydextrose excipient to a powder.

11. The method of claim 9, wherein the alkaloid derivative compound is 1,2,5,6-tetrahydro-1-methyl-3-pyridine carboxaldehyde methyl oxime hydrochloride (CI-979 HCl).

12. The method of claim 9, wherein the cyclic polydextrose excipient is selected from the group consisting of α-cyclodextrin, β-cyclodextrin, δ-cyclodextrin, and hydroxypropyl β-cyclodextrin.

* * * * *